United States Patent
Davis

(10) Patent No.: US 10,780,100 B2
(45) Date of Patent: Sep. 22, 2020

(54) HOMOGENEOUS OPHTHALMIC COMPOSITION

(71) Applicant: Randal Davis, Chattanooga, TN (US)

(72) Inventor: Randal Davis, Chattanooga, TN (US)

( * ) Notice: Subject to any disclaimer, the term of this patent is extended or adjusted under 35 U.S.C. 154(b) by 0 days.

(21) Appl. No.: 16/158,904

(22) Filed: Oct. 12, 2018

(65) Prior Publication Data

US 2019/0070199 A1    Mar. 7, 2019

Related U.S. Application Data

(63) Continuation of application No. 14/846,752, filed on Sep. 5, 2015, now Pat. No. 10,130,639.

(51) Int. Cl.
| | |
|---|---|
| *A61P 27/02* | (2006.01) |
| *A61P 29/00* | (2006.01) |
| *A61K 9/00* | (2006.01) |
| *A61K 31/4709* | (2006.01) |
| *A61K 31/573* | (2006.01) |
| *A61K 31/196* | (2006.01) |
| *A61K 9/08* | (2006.01) |
| *A61K 47/38* | (2006.01) |
| *A61K 47/10* | (2017.01) |
| *A61K 47/18* | (2017.01) |

(52) U.S. Cl.
CPC .......... *A61K 31/573* (2013.01); *A61K 9/0048* (2013.01); *A61K 9/08* (2013.01); *A61K 31/196* (2013.01); *A61K 31/4709* (2013.01); *A61K 47/10* (2013.01); *A61K 47/183* (2013.01); *A61K 47/38* (2013.01)

(58) Field of Classification Search
CPC ...... A61K 9/0048; A61K 9/08; A61K 31/573; A61K 31/196; A61K 31/4709; A61P 27/02; A61P 29/00
See application file for complete search history.

(56) References Cited

U.S. PATENT DOCUMENTS

| | | | |
|---|---|---|---|
| 5,607,942 A | 3/1997 | Petersen et al. | |
| 5,800,807 A | 9/1998 | Hu et al. | |
| 6,716,830 B2 | 4/2004 | Cagle et al. | |
| 7,671,070 B2 | 3/2010 | Cagle et al. | |
| 8,129,431 B2 | 3/2012 | Sawa et al. | |
| 8,669,290 B2 | 3/2014 | Sawa et al. | |
| 8,754,131 B2 | 6/2014 | Sawa et al. | |
| 8,871,813 B2 | 10/2014 | Sawa et al. | |
| 2007/0049552 A1 | 3/2007 | Babu | |
| 2007/0087980 A1* | 4/2007 | Suzuki | A61K 9/08 514/28 |
| 2008/0050335 A1 | 2/2008 | Faour | |
| 2011/0082125 A1 | 4/2011 | Singh | |

OTHER PUBLICATIONS

"Ophthalmic Antibiotic-Steroid Combinations Review," Mar. 1, 2010, Provider Synergies, L.L.C. 2004-2010 (7 pgs.).
Shoss et al., "Postoperative Care in Cataract Surgery," vol. 24, No. 1, Jan. 2013, pp. 66-73, www.co-ophthalmology.com.
Carreno et. al., Clin Opthalmol 2012; 6: 637-644, Apr. 27, 2012.
"Care of the Adult Patient with Cataract: Reference Guide for Clinicians," American Optometric Association, Mar. 1999 (43 pgs.).
Olthoff et al., American. Academy. of Ophthalmology, vol. 112; Jun. 6, 2005. pp. 953-961 and pp. 953 e1-953 37.
Donnenfeld et al., Int Ophthalmol Clin. 2006 Fall; 46(4):21-40.
Freeman et al, Expert Rev. Ophthalmol.. 2009; 4(1): 59-64 (8 pgs.).
Dry Eye Zone: Preservative Reference List, http://www.dryeyezone.com/encyclopedia/preservativeslist.html, Nov. 18, 2014 (4 pgs.).
Hayasaka et. al, Ophthalmic Res. 35, 341-44 (2003) (PubMed Abstract 14688425).
"Intrastromal corneal ring segment SK implantation for moderate to severe keratoconus" by Sansanayudh et al., J. Cataract. Refract. Surg. 36, 110-13 (2010).
"Update on twice-daily bromfenac sodium sesquihydrate to treat postoperative ocular inflammation following cataract extraction" by Carreno et al, Clin. Opthal. 6637-44(2012).

* cited by examiner

*Primary Examiner* — Theodore R. West
(74) *Attorney, Agent, or Firm* — Eric B. Fugett; Mark A. Pitchford; Pitchford Fugett, PLLC

(57) ABSTRACT

This application is directed to a homogeneous solution of an aqueous, topical composition useful for the treatment of infection and/or for the treatment of inflammation due to trauma to tissue. Specifically, this application relates to a homogeneous, aqueous composition of a quinolone antibiotic and an anti-inflammatory agent.

20 Claims, No Drawings

HOMOGENEOUS OPHTHALMIC COMPOSITION

This application is a continuation of U.S. patent application Ser. No. 14/846,752, which was filed Sep. 5, 2015 and issued as U.S. Pat. No. 10,130,639 on Nov. 20, 2018, the entire disclosure of which is hereby incorporated by reference.

BACKGROUND

A cataract is an opaque portion of the lens of the eye. A cataract can be localized to a small region of the lens or it can be diffuse wherein the entire lens appears cloudy. It is the primary cause of visual impairment worldwide, and also the leading cause of vision loss in the United States. An estimated 20.5 million Americans aged 40 years and older have a cataract in one or both eyes. This number is expected to increase to 30.1 million by 2020.

Cataracts can occur at any age and can be present at birth. Causes of cataracts include age, heredity, trauma, inflammation, metabolic disorders, smoking, alcohol consumption, nutritional deficiencies, certain medications, and ultra-violet radiation. Fortunately, cataract surgery is available to reduce this visual impairment.

Cataract surgery involves removal of the entire eye lens with concomitant replacement of the lens with an artificial lens. According to the WHO, the number of cataract surgeries performed in 2010 was estimated to be around 20 million and this number is expected to reach 32 million by 2020. About 3 million cataract surgeries are performed each year in the U.S. alone, making it the most common surgery for Americans over age 65. The amount spent on cataract surgeries in the U.S. is several billion dollars per year.

Proper post-operative care is critical to ensure an optimal visual outcome after cataract surgery. It is during the period of post-operative care that most complications occur, such as bacterial infection, uncontrolled elevated intraocular pressure (IOP), ocular hypertension, malignant glaucoma, wound leakage, cystoid macular edema (CEM), endophthalmitis, iris prolapse, intraocular lens dislocation, hemorrhage, and severe inflammation. The post-operative regimen normally includes restricted activity and the application of a multitude of topical medications to the eye at numerous times per day for 1-8 weeks depending on the patient's situation and the nature of the surgery. These topical medications generally include an antibiotic to be applied 1-4× per day; a steroidal agent to be applied 1-4× per day, and/or a non-steroidal agent to be applied 1-4× per day, with a 5 minute gap between the application of the each medication to the eye. The time gap between doses helps to diminish the likelihood that the first dose will be washed out by the second dose because of insufficient time for absorption of the first dose.

Most people, especially the elderly who undergo the majority of cataract surgeries, experience difficulty in complying with such a complicated medication regimen. For example, it is difficult for some people to put drops in their eyes, which is amplified by the need to do so four times a day with three separate solutions for a total of 1-8 weeks. As mentioned above, there is a problem wash out of the first medicine by application of the second medicine if the required wait time is not adhered to. Another problem is that one or more of the three bottles may be misplaced, contaminated, or damaged. Yet another problem is the difficulty in keeping track of which medicine was already instilled in the eye when there are three bottles of medicine to be used in one sitting. Still another problem is that the length of time the medicating process takes is long because there is a wait time of 5 minutes after each drop is instilled, which process totals about an hour a day devoted to instilling drops to the eye. Also, another problem is that attempts at combining a quinoline antibiotic with an anti-inflammatory agent results in formulations containing a precipitate and/or particulate matter as in a suspension so that there are none commercially available as an aqueous solution.

Thus, there is an urgent need for an easier-to-follow medication regimen in order to increase patient compliance and to ensure better visual outcomes. The composition described in this application solves this problem by combining all three previously separate medications into a single, homogeneous solution, which will be significantly less complicated for the patient to use and will result in better compliance and visual outcomes.

Unexpectedly, preliminary results indicate that use of the composition described herein, which contains all of the active ingredients within one solution, seems to reduce the incidence of cystoid macular edema (CME) more effectively than the use of separate solutions of each of the active ingredients. CME is the most prevalent cause of vision loss after cataract surgery, with up to 58% of patients having some angiographic evidence of CME and there is no reliable treatment for the prevention or treatment of CME following cataract surgery.

SUMMARY

A composition including an aqueous, homogeneous solution of an antibiotic or mixtures thereof and an anti-inflammatory agent or mixtures thereof is disclosed herein. The pH of the composition ranges from 4.5-8.0. In one embodiment, the composition contains 0.5% by weight moxifloxacin hydrochloride, 0.07% bromfenac sodium sesquihydrate, 0.1% by weight dexamethasone sodium phosphate, 0.01% by weight edetate disodium dihydrate, 0.1% by weight hydroxyethyl cellulose, 0.005% by weight benzalkonium chloride, hydrochloric acid to adjust pH, sodium hydroxide to adjust pH, and 1.8% glycerin.

DETAILED DESCRIPTION

The present invention contemplates an aqueous, homogeneous solution of an antibiotic or mixtures thereof and an anti-inflammatory agent or mixtures thereof. Also contemplated is a method of treatment of an ophthalmic, an otic, or a nasal condition by the topical application of the contemplated solution to the affected tissue. The indicated condition may be an infection or an inflammation of tissue or may be for the prevention of post-surgical trauma or infection, i.e., a prophylactic measure. Another contemplated embodiment is a method of making the contemplated solution.

In one embodiment, the solution contains one antibiotic and one anti-inflammatory agent. In another embodiment, the solution contains a mixture of antibiotics and one anti-inflammatory agent. In yet another embodiment, the solution contains one antibiotic and a mixture of anti-inflammatory agents. In still yet another embodiment, the solution contains a mixture of antibiotics and a mixture of anti-inflammatory agents.

The contemplated solution is an aqueous, homogeneous solution and not a suspension. As is generally understood, a solution denotes a homogeneous, transparent liquid that is free of particulate matter, and a suspension denotes an aqueous formulation that contains solid particles and is not homogeneous.

Quite often, the combination of an antibiotic and an anti-inflammatory agent results in precipitate formation so that antibiotic-steroid combinations currently available are in the form of ointments and suspensions. However, both of these forms of medication are problematic for treatment of the eyes in particular. Ophthalmic ointments are cumbersome to use, do not deliver consistent levels of medication, and can impede delivery of other ophthalmic drugs by serving as a physical and chemical barrier due to the presence of the viscous gel vehicle. Ophthalmic suspensions require adequate agitation before use, do not deliver consistent levels of medication, mix with tears less rapidly, and can cause irritation due to the presence of particulates. Also, absorption of both of these forms of medication is minimal.

The concentrations of the antibiotic and the anti-inflammatory agent in the solution will vary depending upon the activity of the particular antibiotic and the nature of the treatment, i.e., infection or prophylactic. In one embodiment, the composition contains about 0.1 to about 1% by weight of the antibiotic or mixtures thereof and about 0.01 to about 1% by weight of the anti-inflammatory agent or mixtures thereof. In another embodiment, the composition contains about 0.5 to about 1% by weight of the antibiotic or mixtures thereof and about 0.1 to about 1% by weight of the anti-inflammatory agent or mixtures thereof. In still another embodiment, the composition contains about 0.5% by weight of the antibiotic or mixtures thereof and about 0.1% by weight of the anti-inflammatory agent or mixtures thereof. When there are mixtures of anti-inflammatory agents in the composition, each of them is present in the range of about 0.07 to about 1% by weight. The pH of the composition ranges from about 4.5 to about 8.0. The pH of the composition can also be from 7.5-8.0.

The present composition contains a quinolone antibiotic, derivatives thereof, salts thereof, or mixtures thereof. Quinolone antibiotics include moxifloxacin, ciprofloxacin, oflaxacin, norfloxacin, lomefloxecin, derivatives thereof, salts thereof, and mixtures thereof. In another embodiment, the antibiotic is moxifloxacin hydrochloride.

The composition also contains an anti-inflammatory agent. Anti-inflammatory agents include a non-steroidal agent, a steroidal agent, or a mixture of a non-steroidal agent and a steroidal agent. In one embodiment, the anti-inflammatory agent comprises a steroidal agent. Common steroidal agents include dexamethasone sodium phosphate, budensonide, triamcinolone, hydrocortisone, loteprednol, prednisolone, mometasone, fluticasone, rimexolone, fluorometholone, beclomethasone, flunisolide, derivatives thereof, and mixtures thereof. In yet another embodiment, the anti-inflammatory agent is dexamethasone sodium phosphate.

In an alternative embodiment, the anti-inflammatory agent comprises a non-steroidal agent. Well-known non-steroidal agents include bromfenac, bromfenac sodium, bromfenac sodium sesquihydrate, aspirin, nabumetome, etodolac, meclofenamate, ibuprofen, flurbiprofen, diffusional, piroxicam, suprofen, diclofenac, sulindac, oxyphenbutazone, oxaproazin, ketorolac, naproxen, nepafenac, bromfenac, mefamic acid, ketoprofen, amfenac, fenoprofen, phenylbutazone, indomethacin, cececoxib, nupafant, filaminast, salts thereof, hydrates thereof, and derivatives thereof. In one embodiment, the anti-inflammatory agent is bromfenac or a pharmaceutically acceptable salt thereof or a hydrate thereof or mixtures thereof. In another embodiment, the anti-inflammatory agent is bromfenac sodium sesquihydrate. In yet another embodiment, the anti-inflammatory agent is bromfenac sodium.

In a different embodiment, the anti-inflammatory agent is a mixture of a non-steroidal agent and a steroidal agent. For example, the anti-inflammatory agent can be a mixture of bromfenac sodium and dexamethasone sodium phosphate. As another example, the anti-inflammatory agent is a mixture of bromfenac sodium sesquihydrate and dexamethasone sodium phosphate.

Thus, one embodiment of the composition can be moxifloxacin hydrochloride and dexamethasone sodium phosphate. Another embodiment of the composition can be moxifloxacin hydrochloride and bromfenac sodium. Yet another embodiment can be moxifloxacin hydrochloride, bromfenac sodium sesquihydrate, and dexamethasone sodium phosphate.

The composition further can contain a pharmaceutically acceptable additive. This additive can be a preservative, a solubility enhancer, a thickener, a pH moderating agent, a buffer, a humectant, or mixtures thereof. Commonly known preservatives are contemplated herein, including a detergent preservative, an oxidizing preservative, and an ionic-buffered preservative. Examples of preservatives are edetate sodium; benzalkonium chloride; centrimonium chloride; sodium perborate; stabilized oxychloro complex; sorbic acid; thimersol; polyquarternium-1; polyhexamethylene biguanide; chlorobutanol; phenylethyl alcohol; methyl paraben; propyl paraben; a combination of boric acid, zinc, sorbital, and propylene glycol; and mixtures thereof.

The composition can also contain a solubility enhancer. Common solubility enhancers include cyclodextrin, polysorbate 20, polysorbate 60, polysorbate 80, Pluronic®, and mixtures thereof.

The present composition can also include a thickener. Examples of thickeners include hydroxyethylcellulose, methyl cellulose, hydroxypropylmethyl cellulose, carboxymethyl cellulose, hydroxypropyl cellulose, polyvinyl alcohol, polyvinylpyrrolidone, and mixtures thereof.

The composition can contain a pH moderating agent. Suitable pH moderating agents are acids and bases such as sodium hydroxide, hydrochloric acid, phosphoric acid, acetic acid, and mixtures thereof.

Buffers can also be included in the composition. Appropriate buffers include boric acid, sodium borate, and mixtures thereof.

Furthermore, the composition can contain a humectant. The humectant can be glycerin, sorbitol, gelatin, mannitol, dextrose, sucrose, urea, and mixtures thereof.

Also contemplated herein is a composition comprising moxifloxacin hydrochloride, dexamethasone sodium phosphate, edetate disodium dihydrate, hydroxyethyl cellulose, benzalkonium chloride, hydrochloric acid to adjust pH, sodium hydroxide to adjust pH, and glycerin.

A composition including 0.5% by weight moxifloxacin hydrochloride, 0.08% by weight bromfenac sodium, 0.1% by weight dexamethasone sodium phosphate, 0.01% by weight edetate disodium dihydrate, 0.1% by weight hydroxyethyl cellulose, 0.005% by weight benzalkonium chloride, hydrochloric acid to adjust pH, sodium hydroxide to adjust pH, and 1.8% by weight glycerin is contemplated herein.

Also, a composition containing 0.5% by weight moxifloxacin hydrochloride, 0.07% bromfenac sodium sesquihydrate, 0.1% by weight dexamethasone sodium phosphate, 0.01% by weight edetate disodium dihydrate, 0.1% by weight hydroxyethyl cellulose, 0.005% by weight benzalkonium chloride, hydrochloric acid to adjust pH, sodium hydroxide to adjust pH, and 1.8% glycerin is contemplated herein.

In addition, a composition containing 0.5% by weight moxifloxacin hydrochloride, 0.1% by weight dexamethasone sodium phosphate, 0.01% edetate disodium dihydrate, 0.1% by weight hydroxyethyl cellulose, 0.005% by weight benzalkonium chloride, hydrochloric acid to adjust pH, sodium hydroxide to adjust pH, and 1.8% by weight glycerin is considered here.

The composition can be designed for a range of osmolalities though iso-osmolal is the norm. Osmolalities range from about 175 to about 330 mOsm/kg. In one embodiment, the osmolality ranges from 280 to 325 mOsm/kg. The osmolality can be adjusted by the addition of salt such as sodium chloride or potassium chloride or by the use of monosaccharides.

Furthermore, a method of treating an ophthalmic infection or inflammation is contemplated herein. One method entails topically applying an aqueous, homogeneous solution made of an antibiotic or mixtures thereof and an anti-inflammatory agent or mixtures thereof to the eye. In one embodiment, the antibiotic is moxifloxacin hydrochloride and the anti-inflammatory agent is dexamethasone sodium phosphate. In another embodiment, the antibiotic is moxifloxacin hydrochloride and the anti-inflammatory agent is bromfenac sodium. In yet another embodiment, the antibiotic is moxifloxacin hydrochloride and the anti-inflammatory agent is a mixture of bromfenac sodium and dexamethasone sodium phosphate. The aqueous, homogeneous solution of an antibiotic or mixtures thereof and an anti-inflammatory agent or mixtures thereof can be applied topically to the eye once a day, twice a day, three times a day, or four times a day as needed with variable durations of therapy ranging from 1-8 weeks or longer.

Moreover, a method of making an ophthalmic solution is contemplated herein. One method entails dissolving moxifloxacin, dexamethasone, and sodium bromfenac each in separate receptacles of water with stirring to form three aqueous compositions; the pH of each of the compositions is adjusted to pH 7.5-8; then hydroxyethylcellulose is added to the dexamethasone composition with stirring, followed by the addition of glycerin to the dexamethasone composition with stirring; followed by the addition of benzalkonium chloride to the dexamethasone composition with stirring; followed by the addition of edetate disodium to the dexamethasone composition with stirring. The pH is adjusted to pH 7.5-8. Next, the dexamethasone composition is added to the moxifloxacin composition to form a dexamethasone and moxifloxacin composition; then, the sodium bromfenac composition is added to the dexamethasone and moxifloxacin composition with stirring. In an alternative embodiment, sodium bromfenac sesquihydrate can be substituted for sodium bromfenac.

In another method, moxifloxacin and dexamethasone are dissolved in separate receptacles of water with stirring to form two aqueous compositions; the pH of each of the compositions is adjusted to pH 7.5-8; then hydroxyethylcellulose is added to the dexamethasone composition with stirring, followed by the addition of glycerin to the dexamethasone composition with stirring; followed by the addition of benzalkonium chloride to the dexamethasone composition with stirring; followed by the addition of edetate disodium to the dexamethasone composition with stirring. Next, the dexamethasone composition is added to the moxifloxacin composition to form a dexamethasone-moxifloxacin composition.

The order of addition of the additives can be varied and what solution they are added to can be varied also as long as the pH of the solution containing the active ingredients is from 7.5 to 8.0 and the pH of the final solution is from 7.5 to 8.0.

EXAMPLES

Example 1

The following procedure was followed to make a homogeneous, aqueous solution of moxifloxacin, sodium bromfenac, and dexamethasone.
Ingredients
moxifloxacin hydrochloride powder 5.45 g
bromfenac sodium powder 0.805 g
dexamethasone sodium phosphate powder 1 g
edetate disodium dihydrate powder 0.1 g
hydroxyethylcellulose powder (CPS5000) 1 g
benzalkonium chloride solution (0.5%/ml) 5 ml
glycerin 18.2 ml
hydrochloric acid (10% solution) for pH adjustment
sodium hydroxide (1% solution) for pH adjustment
sterile water up to 1000 ml Preliminary attempts to combine the dry active ingredients moxifloxacin and sodium bromfenac and dexamethasone into one aqueous solution by dissolving in water resulted in solubility problems. The resulting mixture appeared hazy with particles visible to the naked eye, where the particles settled on the bottom of the receptacle.

Therefore, the active ingredients moxifloxacin hydrochloride, sodium bromfenac, and dexamethasone sodium phosphate, were weighed out separately and placed into individual clear receptacles. About 300 ml sterile water was added to each receptacle with stirring. All three active ingredients dissolved well to form three transparent solutions. The pH of each of the solutions was then adjusted to pH 7.7-8.0 with hydrochloric acid or sodium hydroxide dropwise. Next, hydroxyethylcellulose was added to the dexamethasone solution with stirring, followed by the addition of glycerin, benzalkonium chloride, and edetate disodium dehydrate, each with stirring afterwards. The pH of each of the solutions was then adjusted to pH 7.7-8.0 with hydrochloric acid or sodium hydroxide dropwise. This dexamethasone solution was then added to the moxifloxacin solution with stirring to form a moxifloxacin and dexamethasone solution. The pH was adjusted to 7.8 as needed. Next, the sodium bromfenac solution was added to the moxifloxacin and dexamethasone solution. The pH was adjusted to 7.8 as needed. The volume was brought up to 1000 ml with sterile water. The solution was clear and transparent. The solution was aseptically filtered and placed into 5 ml sterile droptainers. Testing such as rapid scan for sterility, pyrogenicity, and potency were carried out.

Example 2

The following procedure was followed to make a homogeneous, aqueous solution of moxifloxacin and dexamethasone.
Ingredients
moxifloxacin hydrochloride powder 5.45 g
dexamethasone sodium phosphate powder 1 g
edetate disodium dihydrate powder 0.1 g
hydroxyethylcellulose powder (CPS5000) 1 g
benzalkonium chloride solution (0.5%/ml) 5 ml
glycerin 18.2 ml hydrochloric acid (10% solution) for pH adjustment
sodium hydroxide (1% solution) for pH adjustment
sterile water up to 1000 ml The active ingredients moxifloxacin hydrochloride and dexamethasone sodium phosphate were weighed out separately and placed into individual clear receptacles. About 300 ml sterile water was added with stirring. Both active ingredients dissolved well to form transparent solutions. The pH of each of the solutions was then adjusted to pH 7.7-8.0 with hydrochloric acid or sodium hydroxide dropwise. Next, hydroxyethylcellulose was added to the dexamethasone solution with stirring, followed by the addition of glycerin, benzalkonium chloride, and edetate disodium dehydrate, each with stirring afterwards. The pH was adjusted to 7.8 as needed. This dexamethasone solution was then added to the moxifloxacin solution with stirring to form a moxifloxacin and dexamethasone solution. The pH was adjusted to 7.8 as needed. The volume was brought up to 1000 ml with sterile water. The solution was clear and transparent. The solution was aseptically filtered and placed into 5 ml sterile droptainers. Testing such as rapid scan for sterility, pyrogenicity, and potency were carried out.

Example 3

The following procedure was followed to make a homogeneous, aqueous solution of moxifloxacin, sodium bromfenac sesquihydrate, and dexamethasone.
    Ingredients
    moxifloxacin hydrochloride powder 5.45 g
    bromfenac sodium sesquihydrate powder 0.805 g
    dexamethasone sodium phosphate powder 1 g
    edetate disodium dihydrate powder 0.1 g
    hydroxyethylcellulose powder (CPS5000) 1 g
    benzalkonium chloride solution (0.5%/ml) 5 ml
    glycerin 18.2 ml
    hydrochloric acid (10% solution) for pH adjustment
    sodium hydroxide (1% solution) for pH adjustment
    sterile water up to 1000 ml Preliminary attempts to combine the dry active ingredients moxifloxacin and sodium bromfenac sesquihydrate and dexamethasone into one aqueous solution resulted in significant solubility issues. The resulting mixture appeared hazy with significant particles visible to the naked eye, which settled on the bottom of the receptacle.

Therefore, the active ingredients were weighed out separately and placed into individual clear receptacles. About 300 ml sterile water was added with stirring. All three active ingredients dissolved well to form three transparent solutions. The pH of each of the solutions was then adjusted to pH 7.7-8.0 with hydrochloric acid or sodium hydroxide dropwise. Next, hydroxyethylcellulose was added to the dexamethasone solution with stirring, followed by the addition of glycerin, benzalkonium chloride, and edetate disodium dehydrate, each with stirring afterwards. The pH of each of the solutions was then adjusted to pH 7.7-8.0 with hydrochloric acid or sodium hydroxide dropwise. This dexamethasone solution was then added to the moxifloxacin solution with stirring to form a moxifloxacin and dexamethasone solution. The pH was adjusted to 7.8 as needed. Next, the sodium bromfenac sesquihydrate solution was added to the moxifloxacin-dexamethasone solution. The pH was adjusted to 7.8 as needed. The volume was brought up to 1000 ml with sterile water. The solution was clear and transparent. The solution was aseptically filtered and placed into 5 ml sterile droptainers. Testing such as rapid scan for sterility, pyrogenicity, and potency were carried out.

Example 4

The solutions were analyzed by LCMS and standard curve analysis to confirm the identity and quantity of each active ingredient and are summarized below. Separate stock solutions of moxifloxacin HCl, dexamethasone, and sodium bromfenac were used as standards. Three different samples of solutions containing the three active ingredients, i.e., moxifloxacin HCl, dexamethasone, and sodium bromfenac were analyzed for the concentration of moxifloxacin in solution, the concentration of dexamethasone in solution, and the concentration of sodium bromfenac in solution.
Concentration in Solution
moxifloxacin HCl 5.458±0.211 mg/ml
dexamethasone sodium phosphate 1.102+0.011 mg/ml
bromfenac sodium 0.757+0.047 mg/ml Example 5

The pre-treatment regimen for patients who will undergo cataract surgery is one drop applied to the eye per day for each of three days immediately prior to surgery. The post-treatment regimen is one drop applied to the eye four times a day for fourteen days, including the day of surgery. In some cases, patients have continued the post-treatment regimen for an additional seven days. In one clinical trial, the use of the composition of the present application appears to have eliminated the incidence of CME, which is the most prevalent complication following cataract surgery.

What is claimed is:
1. A method of making an aqueous homogeneous ophthalmic solution comprising:
    adding a quinolone antibiotic to a first receptacle of water to form a first aqueous composition;
    adding a steroidal anti-inflammatory agent to a second receptacle of water to form a second aqueous composition;
    adding a non-steroidal anti-inflammatory agent to a third receptacle of water to form a third aqueous composition;
    combining the first, second, and third aqueous compositions to form an aqueous homogeneous ophthalmic solution having a pH of from about 7.5 to about 8.5;
    wherein the aqueous homogeneous ophthalmic solution remains a solution during topical application to an eye of a patient.
2. The method of claim 1, wherein combining the first, second, and third aqueous compositions comprises:
    combining any two of the first, second, and third aqueous compositions to form an intermediate composition, and
    then combining the remaining aqueous composition with the intermediate composition to form the aqueous homogeneous ophthalmic solution.
3. The method of claim 2, wherein:
    the two aqueous compositions combined to form the intermediate composition are the first and second aqueous compositions; and
    the remaining aqueous composition combined with the intermediate composition to form the aqueous homogeneous ophthalmic solution is the third aqueous composition.
4. The method of claim 1, further comprising adjusting a pH of the first, second, and third aqueous compositions to within the range of about 7.5 to about 8.5 before combining any of the aqueous compositions.

5. The method of claim 4 wherein the adjusted pH of the first, second, and third aqueous compositions differ by no more than 0.3.

6. The method of claim 1, wherein the quinolone antibiotic is selected from the group consisting of moxifloxacin, ciprofloxacin, oflaxacin, norfloxacin, lomefloxecin, derivatives thereof, salts thereof, and mixtures thereof.

7. The method of claim 1, wherein the quinolone antibiotic is moxifloxacin or moxifloxacin hydrochloride.

8. The method of claim 1, wherein the steroidal anti-inflammatory agent is selected from the group consisting dexamethasone sodium phosphate, budensonide, triamcinolone, hydrocortisone, loteprednol, prednisolone, mometasone, fluticasone, rimexolone, fluorometholone, beclomethasone, flunisolide, derivatives thereof, and mixtures thereof.

9. The method of claim 1, wherein the steroidal anti-inflammatory agent is dexamethasone or dexamethasone sodium phosphate.

10. The method of claim 1, wherein the non-steroidal anti-inflammatory agent is selected from the group consisting of bromfenac, bromfenac sodium, bromfenac sodium sesquihydrate, aspirin, nabumetome, etodolac, meclofenamate, ibuprofen, flurbiprofen, diffusional, piroxicam, suprofen, diclofenac, sulindac, oxyphenbutazone, oxaproazin, ketorolac, naproxen, nepafenac, bromfenac, mefamic acid, ketoprofen, amfenac, fenoprofen, phenylbutazone, indomethacin, cececoxib, nupafant, filaminast, salts thereof, hydrates thereof, and derivatives thereof.

11. The method of claim 1, wherein the non-steroidal anti-inflammatory agent is bromfenac sodium or bromfenac sodium sesquihydrate.

12. The method of claim 1, further comprising:
adding at least one compound selected from the group consisting of a preservative, a thickener, a buffer, a humectant, and mixtures thereof to one or more of the first, second, or third aqueous compositions; and
adjusting the pH of the aqueous solution to which the compound is added to within the range of about 7.5 to about 8.5.

13. The method of claim 12, wherein:
the preservative is selected from the group consisting of edetate sodium, benzalkonium chloride, centrimonium chloride, sodium perborate, stabilized oxychloro complex, sorbic acid, thimersol, polyquarternium-1, polyhexamethylene biguanide, chlorobutanol, phenylethyl alcohol, methyl paraben, propyl paraben, a combination of boric acid, zinc, sorbital, and propylene glycol, and mixtures thereof;
the thickener is selected from the group consisting of hydroxyethylcellulose, methyl cellulose, hydroxypropylmethyl cellulose, carboxymethyl cellulose, hydroxypropyl cellulose, polyvinyl alcohol, polyvinylpyrrolidone, and mixtures thereof;
the buffer is selected from the group consisting of boric acid, sodium borate, and mixtures thereof; and
the humectant is selected from the group consisting of glycerin, hyaluronic acid, sorbitol, gelatin, mannitol, dextrose, sucrose, urea, and mixtures thereof.

14. The method of claim 1, further comprising adding hydroxyethylcellulose, benzalkonium chloride, and edetate disodium to the second aqueous composition, and then adjusting the pH of the second aqueous composition to within the range of about 7.5 to about 8.5 before combining any of the aqueous compositions.

15. A method of making an aqueous homogeneous ophthalmic solution, comprising:
dissolving moxifloxacin or moxifloxacin hydrochloride in a first receptacle of water with agitation to form an aqueous moxifloxacin composition;
dissolving dexamethasone or dexamethasone sodium phosphate in a second receptacle of water with agitation to form an aqueous dexamethasone composition;
dissolving bromfenac sodium or bromfenac sodium sesquihydrate in a third receptacle of water with agitation to form an aqueous bromfenac composition;
adding one or more of a preservative, a thickener, a buffer, and a humectant to one or more of the aqueous moxifloxacin, dexamethasone, and bromfenac compositions with agitation;
ensuring that each of the aqueous moxifloxacin, dexamethasone, and bromfenac compositions has a pH of from about 7.5 to about 8.5;
adding the aqueous sodium bromfenac composition to the aqueous moxifloxacin composition with agitation to form an intermediate composition; and
adding the aqueous dexamethasone composition to the intermediate composition with agitation to form an aqueous homogeneous ophthalmic solution.

16. The method of claim 15, wherein the aqueous homogeneous ophthalmic solution has a pH in the range of about 7.5 to about 8.5 and remains a solution during topical application to an eye of a patient.

17. The method of claim 15, wherein the adding one or more of a preservative, a thickener, a buffer, and a humectant to one of the aqueous moxifloxacin, dexamethasone, or bromfenac compositions with agitation is adding hydroxyethylcellulose, glycerin, and edetate disodium to the aqueous dexamethasone composition.

18. The method of claim 15, further comprising adding benzalkonium chloride to the aqueous homogeneous ophthalmic solution.

19. A method of making an aqueous homogeneous ophthalmic solution, the method consisting of:
adding an amount of moxifloxacin hydrochloride to a first receptacle of water to form a first aqueous composition;
adding an amount of dexamethasone sodium phosphate to a second receptacle of water to form a second aqueous composition;
adding an amount of bromfenac sodium to a third receptacle of water to form a third aqueous composition;
adding one or more of a preservative, a thickener, a buffer, a chelator, and a humectant to one or more of the first, second, and third aqueous compositions;
adjusting a pH of each of the first, second, and third aqueous compositions as needed to bring the pH of each aqueous composition within the range of 7.5 to 8.5;
after adjusting the pH of each of the aqueous compositions, then combining the first and second aqueous compositions to form an intermediate composition; and
combining the third aqueous composition with the intermediate composition to form an aqueous homogeneous ophthalmic solution;
wherein the aqueous homogeneous ophthalmic solution has a pH in the range of 7.5 to 8.5 and remains a solution during topical application to an eye of a patient.

20. The method of claim 19, wherein the aqueous homogeneous ophthalmic solution has:
a concentration of moxifloxacin hydrochloride of from 5.247 to 5.669 mg/ml, and a concentration of dexamethasone sodium phosphate of from 1.091 to 1.113 mg/ml.

\* \* \* \* \*